(12) United States Patent
Ruediger et al.

(10) Patent No.: US 6,653,290 B2
(45) Date of Patent: Nov. 25, 2003

(54) TUMOR PROLIFERATION INHIBITORS

(75) Inventors: Edward H. Ruediger, Quebec (CA); Neelakantan Balasubramanian, Madison, CT (US); Mikael Mahler, Outremont (CA); Carol Bachand, Candiac (CA); Francis Beaulieu, Laprairie (CA)

(73) Assignee: Bristol-Myers Squibb Company, Princeton, NJ (US)

( * ) Notice: Subject to any disclaimer, the term of this patent is extended or adjusted under 35 U.S.C. 154(b) by 10 days.

(21) Appl. No.: 09/962,181

(22) Filed: Sep. 25, 2001

(65) Prior Publication Data

US 2002/0068705 A1 Jun. 6, 2002

Related U.S. Application Data

(60) Provisional application No. 60/238,712, filed on Oct. 6, 2000.

(51) Int. Cl.$^7$ .......................... A01N 43/04; A61K 31/70
(52) U.S. Cl. .......................... 514/43; 514/42; 436/18.7; 436/22.1; 436/27.1; 436/28.6
(58) Field of Search ............................. 536/18.7, 22.1, 536/28.6, 27.1; 514/42, 43

(56) References Cited

U.S. PATENT DOCUMENTS

| | | | |
|---|---|---|---|
| 4,487,925 A | 12/1984 | Nettleton, Jr. et al. | |
| 4,552,842 A | 11/1985 | Nettleton, Jr. et al. | |
| 4,785,085 A | 11/1988 | Kaneko et al. | |
| 5,043,335 A | 8/1991 | Kleinschroth et al. | |
| 5,407,940 A | 4/1995 | Bisagni et al. | |
| 5,468,849 A | * 11/1995 | Lam et al. ................. | 536/18.5 |
| 5,468,872 A | 11/1995 | Glicksman et al. | |
| 5,475,110 A | 12/1995 | Hudkins et al. | |
| 5,478,813 A | 12/1995 | Okanishi et al. | |
| 5,498,611 A | 3/1996 | Bisagni et al. | |
| 5,618,809 A | 4/1997 | Barrabee et al. | |
| 5,668,271 A | 9/1997 | Kojiri et al. | |
| 5,674,867 A | 10/1997 | Tamaoki et al. | |
| 6,037,468 A | 3/2000 | Wood et al. | |

FOREIGN PATENT DOCUMENTS

| | | | | |
|---|---|---|---|---|
| EP | 0602597 A2 | 12/1993 | | |
| EP | 0545195 B1 | 11/1995 | | |
| EP | 1101770 A | 5/2001 | | |
| WO | WO 89/07105 | 8/1989 | | |
| WO | WO 95/30682 | 11/1995 | | |
| WO | WO 96/04293 | 2/1996 | | |
| WO | WO 96/11933 | * 4/1996 | ......... | C07D/487/04 |
| WO | WO 98/07433 | * 2/1998 | ......... | A61K/31/70 |
| WO | WO 99/02532 | 1/1999 | | |

OTHER PUBLICATIONS

B. B. Shankar, S. W. McCombie, *Tetrahedron Lett.* (1994), 35: 3005.
B. M. Stolz, J. L. Wood, *Tetrahedron Lett.* (1995), 36: 8543.
J. Anizon, et al., *Bioorg. & Med. Chem.* 6: 1597.
S. W. McCombie, et al., *Bioorg. & Med. Chem. Lett.* (1993), 8: 1537.
C. Bailly, et al., *Biochem.*, (1997), 36: 3917.
D. Von Hoff, et al., *Cancer Chemother., Pharmacol.* (1994), 34 (suppl): S41.
T. Yoshinari, et al., *Cancer Research*, (1993), 53: 490.
T. Yoshinari, et al., *Cancer Research*, (1995), 55: 1310.
D.A. Scudiero, et al, *Cancer Reseach*, (1988), 48: 4827.
E.R. Pereira, et al, *J. Med. Chem.*, (1996), 39: 4471.
Greene and Wuts, Protective Groups in Organic Synthesis, 2$^{nd}$ Ed., John Wiley and Sons and McOmie, New York, 1991.
J. L. Wood, et al., *J. Am. Chem. Soc.* (1995), 117: 10413.
J. T. Link, et al., *J. Am. Chem. Soc.* (1996), 118: 2825.
R. Kobayoshi, et al., *J. Am. Chem. Soc.* (1999), 121: 6501.
A. Mazur and G. Hiler, *J. Org. Chem.* (1997), 62: 4471.
K. Nowak, et al., *Roczniki Chem.*, (1969), 43: 1953.
M. Gallant, et al., *J. Org. Chem.*, (1993), 58: 343.
M.S. Motawia, et al., *J. Carbohydrate Chemistry*, (1995), 14(9): 1279.
Halcomb and Danishefsky, *J. Amer Chem. Soc.*, (1989) 111: 6661.
K.C. Nicolau, et al., *J. Amer Chem. Soc.*, (1989) 111: 6666.
S. F. Vice, et al., *Bioorg. Med. Chem. Lett.* (1994), 4: 1333.
T. Hayashi, et al., *Bioorganic And Medicinal Chemistry*, (1997), 5(3): 497.
Weinreb, et al., *Heterocycles* (1984), 21: 309.
Y.–H. Hsiang, et al, *J. Biol. Chem.*, (1985), 260(27): 14873.
Gonzalez, et al., *Farmacia Clinica* (1997), 14: 250.
Long, et al., *American Association for Cancer Research Proceedings* (1997), 38: 75.
Madden, et al., *Cancer Research* (1992), 52: 525.
O'Connor, et al., *Cancer Communications* (1990), 2: 395.
Pollack, et al., *Molecular Pharmacology* (1999), 56: 185.
Prudhomme, M., *Current Medicinal Chemistry* (2000), 7: 1189.

\* cited by examiner

*Primary Examiner*—James O. Wilson
*Assistant Examiner*—Patrick Lewis
(74) *Attorney, Agent, or Firm*—Shah Makujina

(57) ABSTRACT

The present invention concerns novel sugar derivatives of indolocarbazoles and pharmaceutical formulations thereof which exhibit topoisomerase-I activity and are useful in inhibiting the proliferation of tumor cells.

1 Claim, No Drawings

TUMOR PROLIFERATION INHIBITORS

RELATED APPLICATIONS

This application claims priority benefit under Title 35 §119(e) of U.S. provisional Application No. 60/238,712, filed Oct. 6, 2000.

FIELD OF THE INVENTION

The present invention describes substituted sugar derivatives of indolopyrrolocarbazoles which exhibit topoisomerase-I activity and are useful in inhibiting the proliferation of tumor cells.

BACKGROUND

Topoisomerases are vital nuclear enzymes which function to resolve topological dilemmas in DNA, such as overwinding, underwinding and catenation, which normally arise during replication, transcription and perhaps other DNA processes. These enzymes allow DNA to relax by forming enzyme-bridged strand breaks that act as transient gates or pivotal points for the passage of other DNA strands. Topoisomerase-targeting drugs appear to interfere with this breakage-reunion reaction of DNA topoisomerases. In the presence of topoisomerase-active agents, an aborted reaction intermediate, termed a 'cleavable complex', accumulates and results in replication/transcription arrest, which ultimately leads to cell death. The development of topoisomerase I-active agents therefore offers a new approach to the multi-regimental arsenal of therapies currently used in the clinic for the treatment of cancer. An article in *Cancer Chemother. Pharmacol* [1994, 34 (suppl): S 41–S 45] discusses topoisomerase I-active compounds that are in clinical studies and these have been found to be effective clinical anti-tumor agents. Structurally these clinical candidates are related to the alkaloid camptothecin.

Indolo[2,3-a]carbazole alkaloids such as rebeccamycin (U.S. Pat. Nos. 4,487,925 and 4,552,842) and its water-soluble, clinically-active analog, 6-(2-diethylaminoethyl) rebeccamycin (U.S. Pat. No. 4,785,085), are useful antitumor agents which target DNA. Furthermore, fluoroindolocarbazoles (WO 98/07433) have been disclosed as antineoplastic agents with topoisomerase I inhibitory activity. Indolo[2,3-a]carbazole derivatives related to the Rebeccamycin class are disclosed (EP Appl. 0 545 195 B1 and 0,602,597 A2; *Cancer Research* 1993, 53, 490–494; ibid, 1995, 55, 1310–1315) and claimed to exhibit anti-tumor activity; however the major mechanism of action of these derivatives may not be like camptothecin, which acts as a topoisomerase I poison. Related indolocarbazoles are also disclosed (WO 95/30682) and claimed to exhibit anti-tumor activity. Hudkins, et al. have disclosed a series of fused pyrrolocarbazoles (WO 96/11933 and U.S. Pat. No. 5,475,110) and reported in vitro biological activity such as inhibition of neuronal choline acetyltransferase (ChAT) and protein kinase C (PKC) inhibition for some compounds. U.S. Pat. No. 5,468,849 discloses certain fluororebeccamycin analogs as useful antitumor agents, along with a process for their production by fluorotryptophan analog feeding of a rebeccamycin-producing strain of *Saccharothrix aerocolonigenes*, preferably *Saccharothrix aerocolonigenes* C38,383-RK2 (ATCC 39243). Glicksman, et al. disclose indolocarbazole alkaloids (U.S. Pat. No, 5,468,872), while Kojiri, et al. disclose indolopyrrolocarbazoles having a dissacharide substituent (WO 96/04293). Mazur and Hiller report the synthesis of simple 5-hydroxymethyl glycosides (*J. Org. Chem.* 1997, 62, 4471), while Danishefsky, et al (*J. Am. Chem. Soc.* 1996, 118, 2825) describe the synthesis of 5-methoxy substituted sugar derivatives. Despite these reports, there remains the need for novel and potent cytotoxic compounds useful for inhibiting topoisomerase I activity.

SUMMARY OF THE INVENTION

Thus according to a first embodiment of the first aspect of the present invention are provided compounds of Formula (I) and pharmaceutically acceptable salts and solvates thereof, useful for inhibiting topoisomerase I and the proliferation of tumor cells,

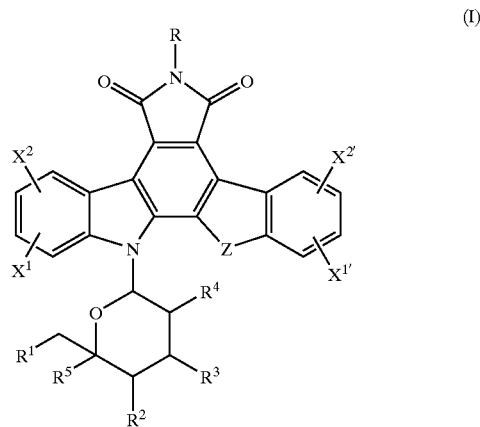

(I)

wherein, $X^1$, $X^{1'}$, $X^2$ and $X^{2'}$ are independently selected from the group consisting of hydrogen, halogen, cyano, $OR^6$, —$CF_3$, alkylcarbonyl, $C_{1-7}$alkyl, nitro, $NR^6R^7$, $SR^6$ and $C(O)OR^6$; wherein said $C_{1-7}$alkyl is optionally substituted with one or more sub stituents selected from the group consisting of halogen, CN, $SR^6$, $OR^6$ and $NR^6R^7$;

Z is selected from the group consisting of NH, O and S;

R is hydrogen, OH, $OC_{1-7}$alkyl, $NH_2$, $N(C_{1-3}$alkyl$)_2$ or $C_{1-7}$alkyl, wherein said $C_{1-7}$alkyl is optionally substituted with one or more substituents selected from the group consisting of halogen, CN, $SR^6$, $OR^6$ and $NR^6R^7$;

$R^1$, $R^2$, $R^3$, and $R^4$ are each independently selected from the group consisting of hydrogen, $C_{1-7}$alkyl, $C_{3-7}$cycloalkyl, halogen, azido, $NR^6R^7$, $NHC(O)NR^6R^7$, $NHC(O)OR^6$, $C(O)OR^6$, $SR^6$ and $OR^6$, wherein said $C_{1-7}$alkyl is optionally substituted with one or more substituents selected from the group consisting of halogen, CN, $SR^6$, $OR^6$ and $NR^6R^7$; and $R^5$ is selected from the group consisting of $C_{1-7}$alkyl, $C_{3-7}$cycloalkyl, halogen, azido, $NR^6R^7$, $NHC(O)NR^6R^7$, $NHC(O)OR^6$, $C(O)OR^6$, $SR^6$ and $OR^6$, wherein said $C_{1-7}$alkyl is optionally substituted with one or more substituents selected from the group consisting of halogen, CN, $SR^6$, $OR^6$ and $NR^6R^7$; and $R^6$ and $R^7$ are independently selected from the group consisting of hydrogen, $C_{1-7}$alkyl and $C_{3-7}$cycloalkyl, wherein said $C_{1-7}$alkyl is optionally substituted with one or more substituents selected from the group consisting of halogen, CN, OH, $OC_{1-3}$alkyl, $NH_2$ or $N(C_{1-3}$alkyl$)_2$; or $R^6$ and $R^7$ together with the nitrogen atom to which they are attached form a non-aromatic 5-8 membered heterocycle containing one or two of the same or different heteroatoms selected from the group consisting of O, N and S.

According to another embodiment of the first aspect of the present invention are provided compounds of Formula (I) wherein R is hydrogen.

According to another embodiment of the first aspect of the present invention are provided compounds of Formula (I) wherein Z is NH.

According to another embodiment of the first aspect of the present invention are provided compounds of Formula (I) wherein $X^1$, $X^{1'}$, $X^2$ and $X^{2'}$ are each F.

According to another embodiment of the first aspect of the present invention are provided compounds of Formula (I) wherein $X^{2'}$ and $X^2$ are each F and $X^1$ and $X^{1'}$ are each H.

According to another embodiment of the first aspect of the present invention are provided compounds of Formula (I) wherein $X^2$ is F and $X^{2'}$, $X^1$ and $X^{1'}$ are each H.

According to another embodiment of the first aspect of the present invention are provided compounds of Formula (I) wherein $X^{2'}$ is F and $X^2$, $X^1$ and $X^{1'}$ are each H.

According to another embodiment of the first aspect of the present invention are provided compounds of Formula (I) wherein $R^1$, $R^2$, $R^3$, $R^4$ and $R^5$ are independently selected from the group consisting of H, OH, F, azido and amino.

Other embodiments of the first aspect of the present invention provide compounds of Formula (I) comprising two or more of the above embodiments of the first aspect suitably combined.

Embodiments of a second aspect of the present invention provide a method for inhibiting tumor growth in a mammalian host which comprises the administration to said host of a tumor-growth inhibiting amount of a compound of the present invention as defined in the embodiments of the first aspect of the invention.

Embodiments of a third aspect of the present invention provide a method for inhibiting tumor growth in a mammalian host which comprises the administration to said host of a tumor-growth inhibiting amount of a pharmaceutical formulation of a compound of the present invention as defined in the embodiments of the first aspect of the invention.

Other embodiments and aspects of the invention will be apparent according to the description provided below.

DETAILED DESCRIPTION OF THE INVENTION

The description of the invention herein should be construed in congruity with the laws and principals of chemical bonding. An embodiment or aspect which depends from another embodiment or aspect, will describe only the variables having values and provisos that differ from the embodiment or aspect from which it depends. Thus, for example, an embodiment which reads "the compound of formula (I) according to the $n^{th}$ aspect of the invention, wherein W is C" should be read to include all remaining variables with values defined in the $n^{th}$ aspect and should be read to further include all the provisos, unless otherwise indicated, pertaining to each and every variable in the $n^{th}$ aspect. The numbers in the subscript after the symbol "C" define the number of carbon atoms a particular group can contain. For example "$C_{1-7}$alkyl" means a straight or branched saturated carbon chain having from one to seven carbon atoms, including without limitation groups such as methyl, ethyl, n-propyl, isopropyl, n-butyl, sec-butyl, isobutyl, t-butyl, n-pentyl, sec-pentyl, isopentyl, n-hexyl and n-heptyl. The term "halogen" includes fluoro, chloro, bromo and iodo.

It is to be understood that the present invention includes any and all possible stereoisomers, geometric isomers, diastereoisomers, enantiomers, conformational isomers and anomers, unless a particular description specifies otherwise.

The numbers in the subscript after the symbol "C" define the number of carbon atoms a particular group can contain. For example "$C_{1-6}$alkyl" means a straight or branched saturated carbon chain having from one to seven carbon atoms including without limitation groups such as methyl, ethyl, n-propyl, isopropyl, n-butyl, sec-butyl, isobutyl, t-butyl, n-pentyl, sec-pentyl, isopentyl, n-hexyl and n-heptyl. "Aryl" means an aromatic hydrocarbon having from six to ten carbon atoms; examples include phenyl and naphthyl. "Substituted aryl" or "substituted aralkyl" means an aryl or aralkyl group independently substituted with one to five (but particularly one to three) groups selected from the group consisting of $C_{1-6}$alkanoyloxy, hydroxy, halogen, $C_{1-6}$ alkyl, trifluoromethyl, $C_{1-6}$alkoxy, $C_{2-6}$alkenyl, $C_{1-6}$alkanoyl, nitro, amino, cyano, azido, $C_{1-6}$ alkylamino and amido. The term "halogen" includes fluoro, chloro, bromo and iodo.

The compounds of this invention can exist in the form of pharmaceutically acceptable salts. Such salts include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds of this invention contain an acidic group, the acidic group can exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. The compounds of the present invention may be hydrated or non-hydrated.

The compounds of this invention can be administered in such oral dosage forms as tablets, capsules (each of which includes sustained release or timed release formulations), pills, powders, granules, elixirs, tinctures, suspensions, syrups and emulsions. The compounds of this invention may also be administered intravenously, intraperitoneally, subcutaneously, or intramuscularly, all using dosage forms well known to those skilled in the pharmaceutical arts. The compounds can be administered alone but generally will be administered with a pharmaceutical carrier selected on the basis of the chosen route of administration and standard pharmaceutical practice. Compounds of this invention can also be administered in intranasal form by topical use of suitable intranasal vehicles, or by transdermal routes, using transdermal skin patches. When compounds of this invention are administered transdermally the dosage will be continuous throughout the dosage regimen.

One aspect of the present invention involves administration of the compounds of the present invention, or pharmaceutically acceptable salts or solvates thereof, to a mammal implanted with a tumor or susceptible to cancer formation. In general the compound would be given in a dose range of from about 0.1 mg/kg to about the MTD (maximum tolerated dose). The dosage and dosage regimen and scheduling of a compound of the present invention must in each case be carefully adjusted, utilizing sound professional judgment and considering the age, weight and condition of the recipient, the route of administration and the nature and extent of the cancer disease condition. The term "systemic administration" as used herein refers to oral sublingual, buccal, transnasal, transdermal, rectal, intramascular, intravenous, intraventricular, intrathecal, and subcutaneous routes. In accordance with good clinical practice, it is preferred to administer the instant compounds at a concentration level which will produce effective beneficial effects without causing any harmful or untoward side effects.

DESCRIPTION OF THE SPECIFIC EMBODIMENTS

Procedures for the preparation of compounds of Formula (I) are illustrated in Schemes 1-5 and the preparation of the key intermediates/starting materials is illustrated in Scheme 6.

SCHEME 1
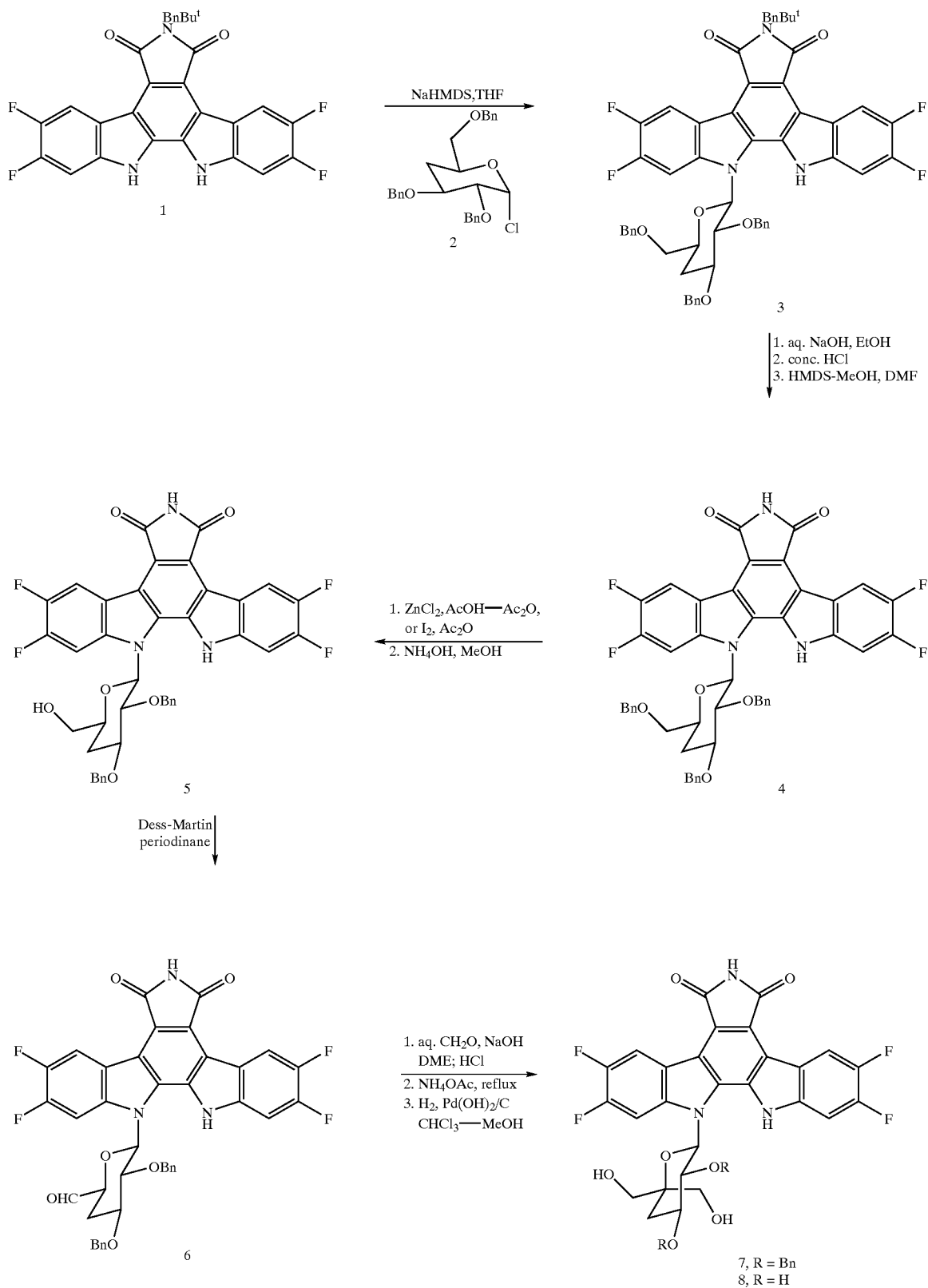

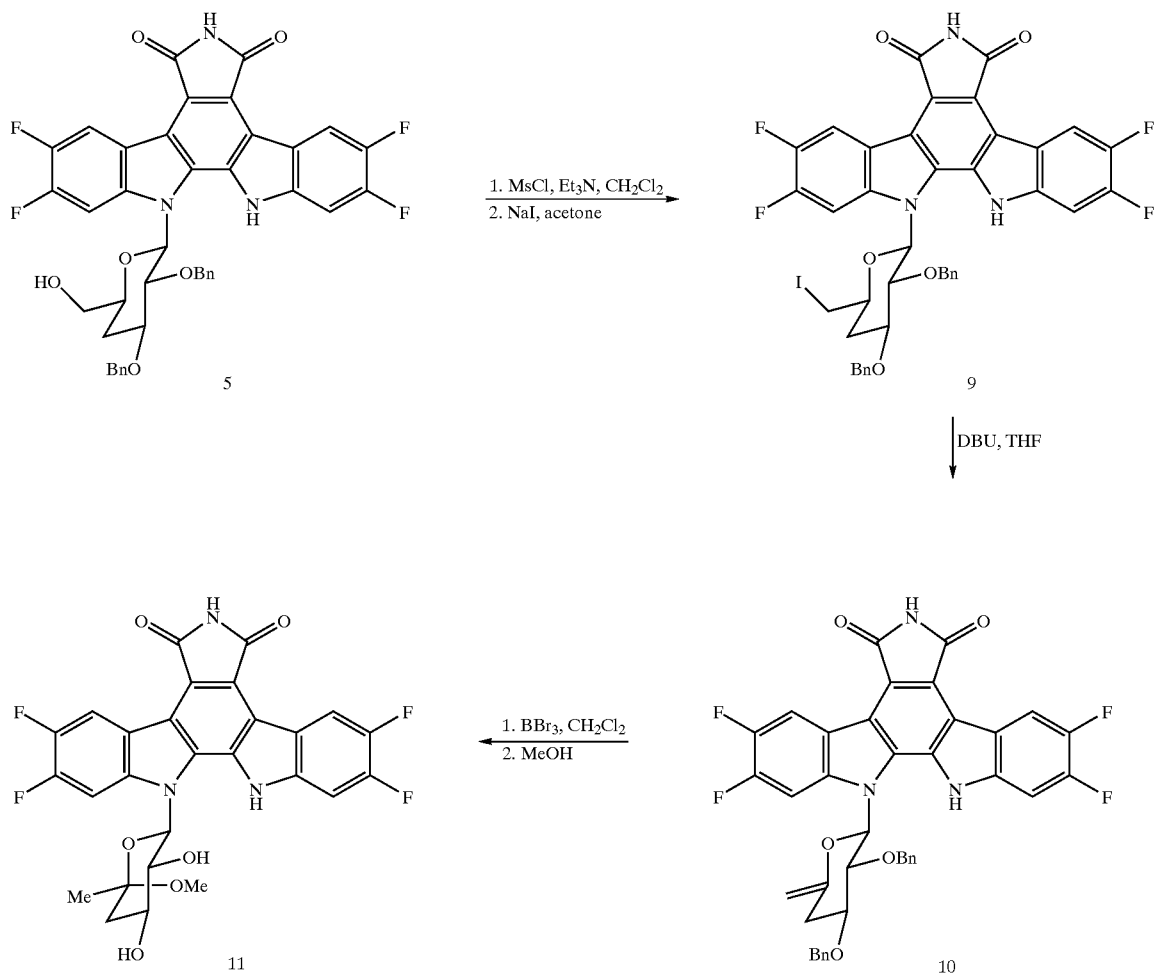
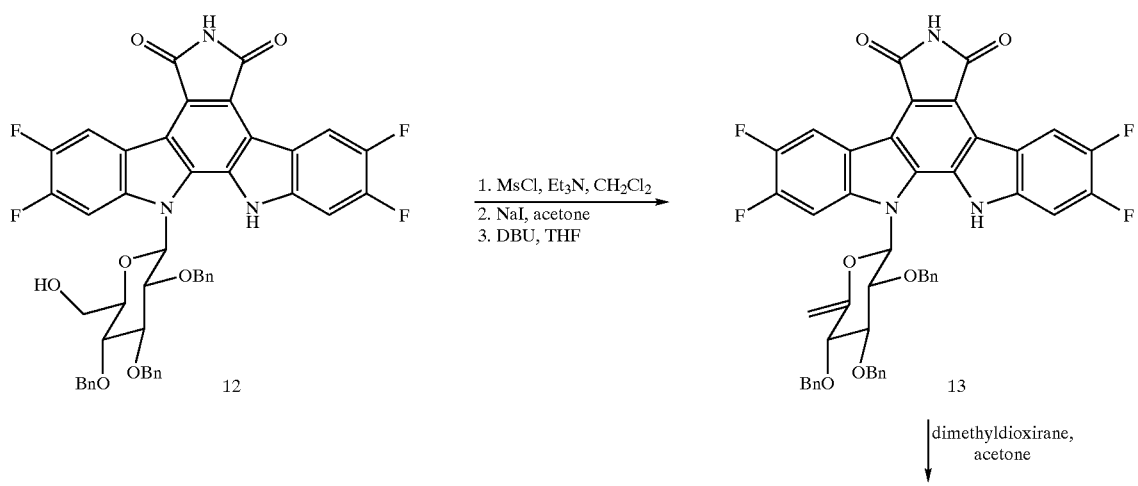

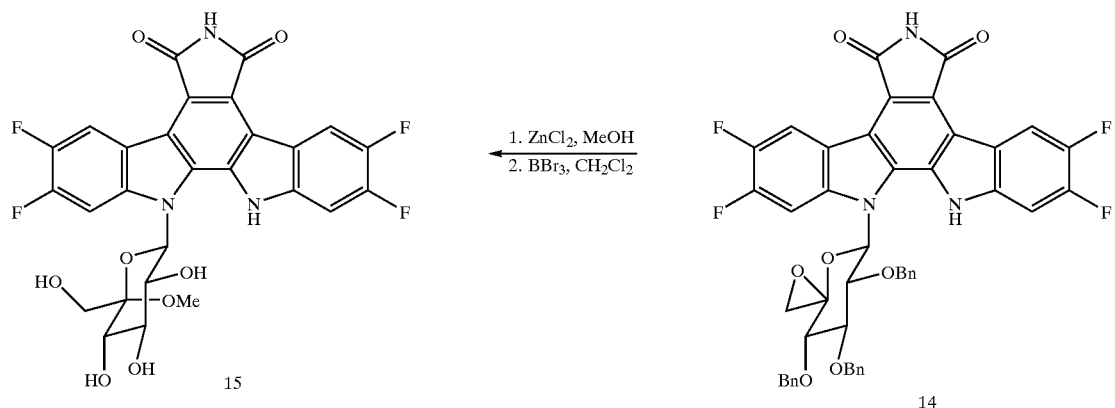
SCHEME 4
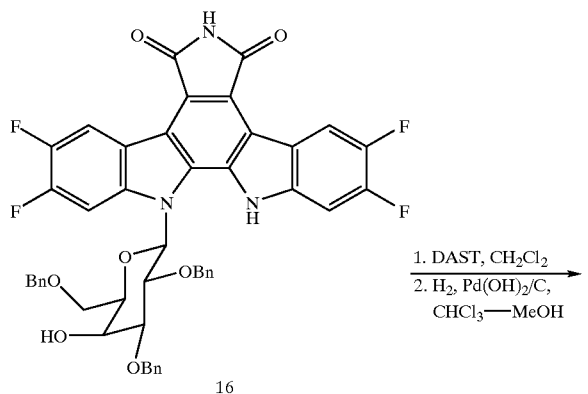
SCHEME 5
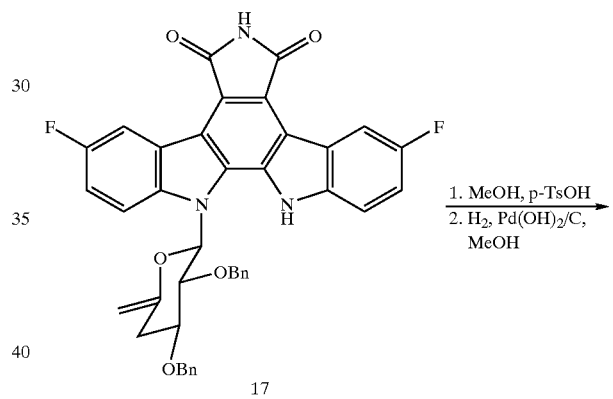
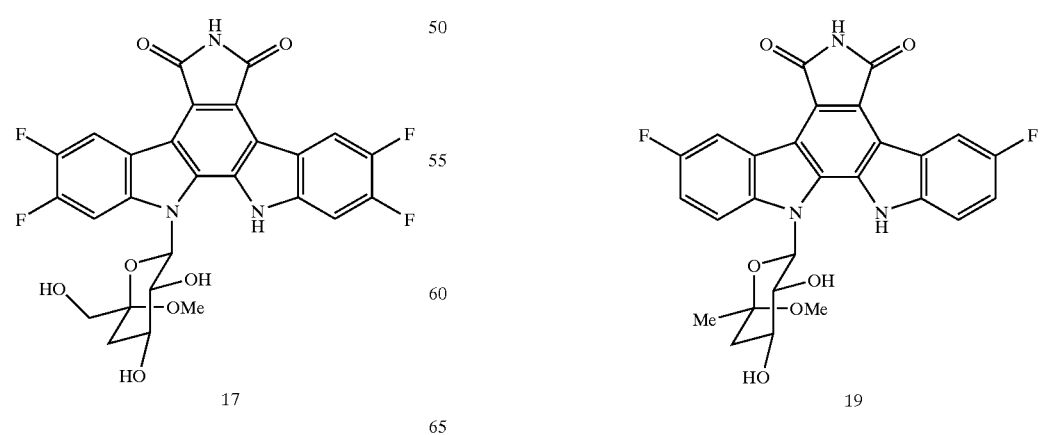

SCHEME 6

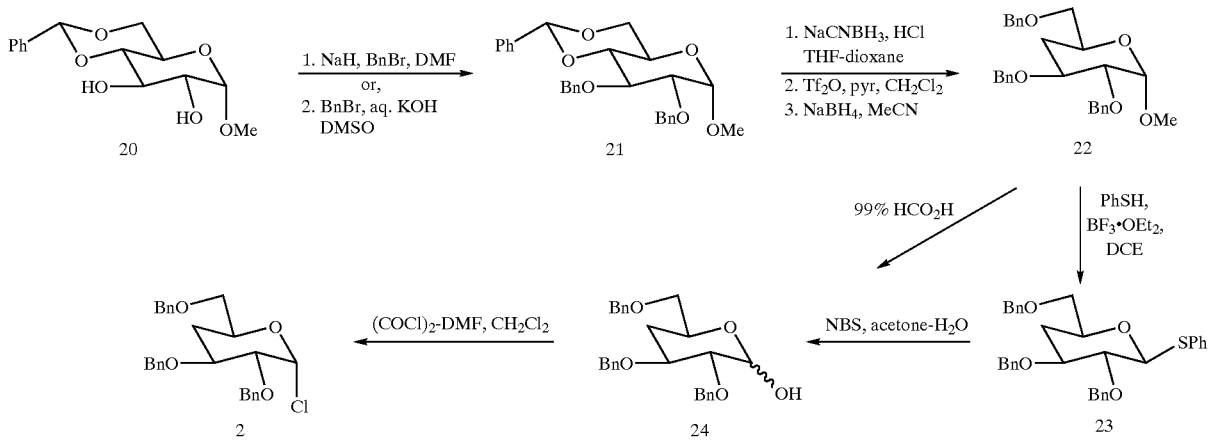

In Scheme 1, the mono- or dianion of 1 was generated using a suitable base, such as sodium hexamethyldisilazide, and was glycosylated with a chlorosugar derivative like 2 to give a protected glycoside (3). Deprotection of the imide moiety was done by base-induced hydrolysis, followed by acidification to give an intermediate anhydride. The latter was conveniently converted to an imide using a suitable amine, such as that provided by reaction with a mixture of hexamethyldisilazane and methanol in dimethylformamide (cf. P. D Davis, R. A. Bit *Tetrahedron Lett.* 1990, 31, 5201). Selectively deprotected glycosides like 5 and 12 could then be prepared by treatment of the corresponding perbenzylated glycosides with zinc chloride in acetic acid-acetic anhydride (cf F. Kong, et al. *Tetrahedron Lett.* 1997, 38, 6725) or with iodine in acetic anhydride (cf K. P. R. Kartha, R. A. Field *Tetrahedron* 1997, 53, 11753), followed by hydrolysis of the intermediate acetates. The resulting primary alcohols could be oxidized under mild conditions, for example using Dess-Martin periodinane or the like, to give the corresponding aldehyde. These aldehydes readily underwent α-hydroxymethylation followed by spontaneous Canizzaro reduction in the presence of aqueous formaldehyde and aqueous sodium hydroxide (cf A. W. Mazur, G. D. Hiler *J. Org. Chem.* 1997, 62, 4471) to give 5'-C-hydroxymethyl-glycosides such as 7. If during the course of this reaction the imide moiety was hydrolyzed to the corresponding anhydride, this was readily converted back to an imide by treatment with a suitable source of ammonia, such as ammonium acetate. Finally, removal of the benzyl protecting groups was then done using a conventional procedure involving hydrogenolysis over Pearlman's catalyst (20% Pd(OH)$_2$ on charcoal), to give a deprotected glycoside (8).

As shown in Scheme 2, the 6'-hydroxyl group of 5 may also be activated, for example as its mesylate and subsequently as the corresponding iodide (9), which may then undergo elimination of the element of HI using a suitable amine base, such as 1,8-diazabicyclo[5.4.0]undec-7-ene (DBU), to give a vinyl ether (10). Subsequent removal of the benzyl protecting groups using boron tribromide, followed by quenching of the reaction mixture with methanol, affords a 5'-C-methoxyglycoside such as 11. Alternatively, as shown for example in Scheme 3, introduction of a 5'-C-methoxy group could precede the final deprotection step. Thus, a vinyl ether (13) can be epoxidized under mild conditions using dimethyldioxirane in acetone (cf S. J. Danishefsky, et al. *J. Am. Chem. Soc.* 1996, 118, 2825), and the resulting epoxide (14) can undergo solvolysis with methanol in the presence of zinc chloride and final deprotection as before to give a 5'-C-methoxyglucoside (15).

Selected examples of 5'-C-methoxyglycosides could also be prepared as shown in Scheme 4. Thus, treatment of a selectively deprotected galactoside (16) with the well-known fluorinating agent DAST [(diethylamino)sulfur trifluoride], followed by debenzylation as before, takes an unexpected course to give predominantly the 5'-C-methoxyglycoside 17.

Alternatively, as shown in Scheme 5, a vinyl ether (18) may be treated with an alcohol, for example methanol, in the presence of a small amount of an acid catalyst, such as p-toluenesulfonic acid, to give a protected 5'-C-alkoxyglycoside. The latter was deprotected as before to give a 5'-C-alkoxyglycoside (e.g., 19).

A key intermediate sugar was prepared as shown in Scheme 6. Conversion of a commercially available methyl-α-D-glucopyranoside (20) to a 4-deoxyglycoside (22) was done as reported by Barrette and Goodman (*J. Org. Chem.* 1984, 49, 176). Deprotection of the anomeric position could be done in two steps, first by treatment with benzenethiol and a Lewis acid, such as boron trifluoride etherate (cf L. A. Paquette, J. A. Oplinger *J. Org. Chem.* 1988, 53, 2953), followed by hydrolysis of the resulting phenylthio sugar derivative (23) using N-bromosuccinimide in a suitable solvent, such as acetone or acetonitrile, in the presence of water (cf B. Fraser-Reid, et al. *J. Am. Chem. Soc.* 1988, 110, 2662). Alternatively, deprotection of the anomeric position could be effected in one step by treatment with a suitable acid, such as 90% formic acid, to give the glucopyranoside (24) directly. Conversion of a glycopyranoside, such as 24, to a glycopyranosyl chloride (2) could be done according to a procedure reported by Iversen and Bundle (*Carb. Res.* 1982, 103, 29).

The compounds which constitute this invention and their methods of preparation will appear more fully from a consideration of the following examples which are given for the purpose of illustration only and are not to be construed as in any way limiting the scope of the invention.

Synthesis of Intermediates

Several intermediate compounds, as well as other conventional starting materials (e.g., 20), used in the preparation of compounds of Formula (I) were generally commercially available. Representative syntheses of some of these compounds are provided hereinbelow nevertheless.

All anhydrous reactions were performed under an atmosphere of nitrogen or argon using either commercially available dry solvents or freshly distilled solvents. Melting points were determined in an open capillary tube with a Thomas- Hoover melting point apparatus and are uncorrected. Column chromatography was performed using EM Science silica gel 60 (230–400 mesh) with the designated solvent system as eluant. Thin-layer chromatography was done on E. Merck silica gel 60 $F_{254}$ plates (0.5 mm). Hplc purity determinations were done using either a Shimadzu LC-10AS with a SPD-10AV UV-V is detector and one of the following columns; YMC Combiscreen ODS-A (4.6×50 mm), or HP Zorbax SB-C18 (4.6×750 mm); or, an HP 1090 DR5 with a diode array detector and a Waters Nova-Pak C18 column (3.9×150 mm). Infrared spectra were recorded on a Nicolet Protégé 460 FTIR as thin films or KBr pellets. $^1$HNMR spectra were recorded on either a Bruker AMX-400 or a Bruker ARX-500 NMR spectrometer and chemical shifts are expressed in parts per million (ppm or δ) with the solvent in use as internal standard. Coupling constants are given in hertz and multiplets are designated as follows; singlet (s), doublet (d), triplet (t), quartet (q), muliplet (m), and broad (br). Low resolution mass spectra were determined on a Finnigan Matt TSQ-7000 triple stage quadrapole spectrometer (positive/negative ESI) operated in the negative ion mode.

EXAMPLE 1

2, 3, 9, 10-Tetrafluoro-12-[5-C-(hydroxymethyl)-4-deoxy-β-D-glucopyranosyl]-indolo[2, 3-a]pyrrolo[3, 4-c]carbazole-5, 7-dione

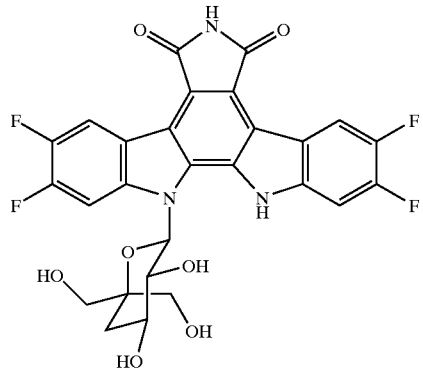

To a solution of Dess-Martin reagent (0.147 g, 0.34 mmol) in 5 mL of dry $CH_2Cl_2$ was added a solution of 2, 3, 9, 10-tetrafluoro-12-(2, 3-di-O-benzyl-4-deoxy-β-D-glucopyranosyl)-indolo[2, 3-a]pyrrolo[3, 4-c]carbazole-5, 7-dione (0.125 g, 0.17 mmol) in 5 mL of dry $CH_2Cl_2$ and the mixture was stirred at room temperature for 2 h. The resulting mixture was diluted with ethyl acetate and then it was washed (sat. $NaHCO_3$, 30%. $Na_2S_2O_3$, brine), dried ($Na_2SO_4$) and evaporated. The crude aldehyde was immediately dissolved in dioxane (6 mL), 37% aqueous formaldehyde (1 mL) and 1 M NaOH (1 mL) were added and the mixture was stirred at room temperature for 18h. The solution was then acidified with 1N HCl and stirred for 4 h. The resulting mixture was diluted with ethyl acetate, washed with water, dried ($Na_2SO_4$) and evaporated to give 2, 3, 9, 10-tetrafluoro-12-[2, 3-di-O-benzyl-4-deoxy-5-C-(hydroxymethyl)-β-D-glucopyranosyl]-indolo-[2, 3-a]furano[3, 4-c]carbazole-5, 7-dione as a yellow gum: MS (ESI$^-$) m/e 753 (M–H)$^-$.

To this crude gum was added ammonium acetate (1.0 g, 13 mmol) and the mixture was heated (oil bath) to reflux for 3 h. The cooled mixture was partitioned with ethyl acetate-water and the organic phase was separated, washed (brine), dried ($Na_2SO_4$) and evaporated to give crude 2, 3, 9, 10-tetrafluoro-12-[2, 3-di-O-benzyl-4-deoxy-5-C-(hydroxymethyl)-β-D-glucopyran-osyl]-indolo[2, 3-a]pyrrolo[3, 4-c]carbazole-5, 7-dione (0.025 g). This material was immediately taken up in 8 mL of methanol-chloroform (1:1), 10% palladium on charcoal (0.025 g) was added and the mixture was hydrogenated at 1 atm for 20 h. The resulting mixture was filtered (Celite), the filtrate was concentrated in vacuo and the residue was chromatographed (hexane-THF, 1:1) to afford the title compound (0.007 g, 7% overall) as a yellow solid: IR (KBr) 3280, 1716, 1700, 1476, 1320 cm$^{-1}$; $^1$H NMR (THF-d$_8$, 400 MHz) δ12.05 (s, 1H), 10.08 (s, 1H), 9.14 (dd, J=11.2, 8.5 Hz, 1H), 9.03 (dd, J=11.2, 8.4 Hz, 1H), 7.76 (dd, J=11.2, 6.6 Hz, 1H), 7.51 (dd, J=10.9, 6.8 Hz, 1H), 6.20 (d, J=9.2 Hz, 1H), 5.68 (m, 1H), 4.48–4.39 (m, 2H), 4.21–4.05 (m, 2H), 4.00 (dd, J=10.9, 4.3 Hz, 1H), 3.90 (dd, J=11.9, 5.8 Hz, 1H), 3.82–3.76 (m, 1H), 3.67–3.60 (m, 2H), 2.14 (dd, J=13.7, 5.3 Hz, 1H), 1.79–1.75 (m, 1H). MS (ESI$^-$) m/e 572 (M–H)$^-$. HPLC: 95.2% (320 nm).

EXAMPLE 2

2, 3, 9, 10-Tetrafluoro-12-(2, 3-di-O-benzyl-4-deoxy-6-iodo-β-D-glucopyranosyl)-6, 7, 12, 13-tetrahydro(5H)indolo[2, 3-a]pyrrolo[3, 4-c]carbazole-5, 7-dione

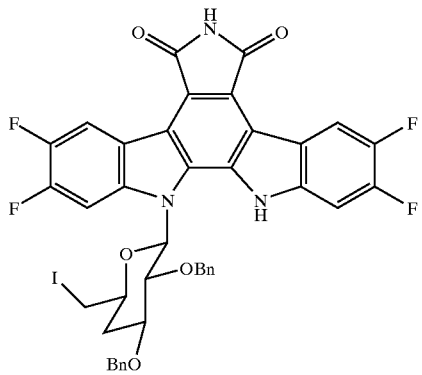

A mixture of 2, 3, 9, 10-tetrafluoro-12-(2, 3-di-O-benzyl-4-deoxy-β-D-glucopyranosyl)-6, 7, 12, 13-tetrahydro(5H) indolo[2, 3-a]pyrrolo[3, 4-c]carbazole-5, 7-dione (2.00 g, 2.76 mmol) and freshly activated and pulverized 4A molecular sieves (0.60 g) in 100 mL of dichloromethane was cooled at 5C. under Ar and triethylamine (0.77 mL, 5.52 mmol), DMAP (0.20 g, 1.64 mmol) and methanesulfonyl chloride (0.32 mL, 4.14 mmol) were added sequentially. The mixture was stirred at the same temperature for 2 h and then it was filtered and the filter-cake was washed with ethyl acetate. The flitrate was diluted with ethyl acetate (200 mL) and ether (50 mL) and then it was washed ($H_2O$×2, brine), dried ($MgSO_4$) and evaporated to give a yellow glass. This material was taken up in 100 mL of acetone, NaI ( ) was added and the mixture was heated to reflux under Ar for 18 h. The cooled mixture was then evaporated to dryness and the residue was taken up in 10 mL of ethyl acetate, washed ($H_2O$×2, brine) dried ($MgSO_4$) and evaporated. The resulting solid was chromatographed ($SiO_2$/2–32% ethyl acetate-hexane) to give the title compound (0.90 g, 39%) as an amorphous yellow solid: $^1$H NMR (CDCl$_3$, 400 MHz) δ10.17 (s, 1H), 9.10 (dd, J=10.6, 8.4 Hz, 1H), 9.02 (dd, J=10.6, 8.5 Hz, 1H), 7.55 (m, 2H), 7.35 (m, 6H), 6.92 (t, J=7.4 Hz, 1H), 6.76 (t, J=7.6 Hz, 2H), 6.20 (d, J=7.6 Hz, 2H), 5.75 (d, J=9.2 Hz, 1H), 4.77 and 4.71 (ab q, J=11.5 Hz, 2H), 4.13 (m, 2H), 3.99 (t, J=8.7 Hz, 1H), 3.80 (m, 2H 3.63 (d, J=9.0 Hz, 1H), 3.48 (d, J=10.8 Hz, 1H), 2.42 (m, 1H), 2.32 (m, 1H). MS (ESI$^-$) m/e 832 (M–H)$^-$.

EXAMPLE 3

2, 3, 9, 10-Tetrafluoro-12-(2, 3, 4-tri-O-benzyl-6-iodo-β-D-glucopyranosyl)-6, 7, 12, 13-tetrahydro(5H)indolo[2, 3-a]pyrrolo[3, 4-c]carbazole-5, 7-dione

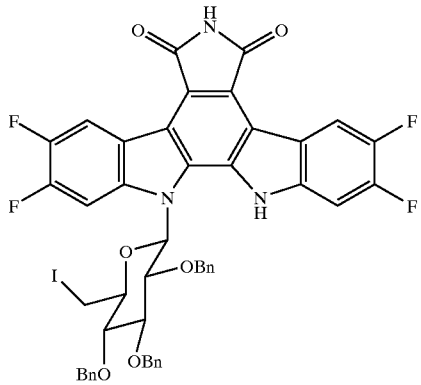

Prepared as described for Example 2 as a yellow solid in 69% yield: $^1$H NMR (acetone-d$_6$, 400 MHz) δ10.13 (s, 1H), 9.03 (dd, J=10.6, 8.3 Hz, 1H), 8.95 (dd, J=10.6, 8.3 Hz, 1H), 7.85 (s, 1H), 7.52 (dd, J=10.2, 6.5 Hz, 1H), 7.48–7.29 (m, 11H), 6.95 (t, J=7.4 Hz, 1H), 6.80 (t, J=7.6 Hz, 2H), 6.16 (d, J=7.2 Hz, 2H), 5.84 (d, J=8.5 Hz, 1H), 5.62 (dd, J=5.9, 1.9 Hz, 2H), 5.16 and 5.05 (ab q, J=10.7 Hz, 2H), 4.90 (s, 2H), 4.15–3.67 (m, 5H), 3.24 (d, J=10.6 Hz, 1H). MS (ESI$^-$) m/e 938 (M–H)$^-$.

EXAMPLE 4

2, 3, 9, 10-Tetrafluoro-12-(2, 3-di-O-benzyl-4, 6-dideoxy-5, 6-anhydro-β-D-glucopyranosyl)-6, 7, 12, 13-tetrahydro(5H)indolo[2, 3-a]pyrrolo[3, 4-c]carbazole-5, 7-dione

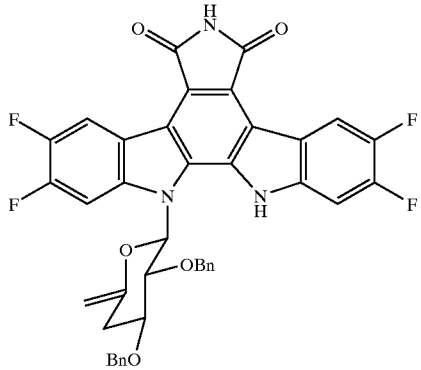

To an ice-cold solution of 2, 3, 9, 10-tetrafluoro-12-(2, 3-di-O-benzyl-4-deoxy-6-iodo-β-D-glucopyranosyl)-6, 7, 12, 13-tetrahydro(5H)indolo[2, 3-a]pyrrolo[3, 4-c]-carbazole-5, 7-dione (0.500 g, 0.60 mmol) in 20 mL of dry THF was added DBU (0.27 mL, 1.80 mmol) and the solution was kept at 5C. for 2 h. The cooling bath was then removed and stirring was continued at room temperature for 16 h. Another portion of DBU (0.27 mL, 1.80 mmol) was then added and the reaction was allowed to continue for another 24 h. A further portion of DBU (0.27 mL, 1.80 mmol) was added and stirring was continued for an additional 24 h. The resulting mixture was diluted with ethyl acetate and then it was washed (1 N HCl×2, H$_2$O×2, 1 M NaHCO$_3$×2, H$_2$O, brine), dried (MgSO$_4$) and evaporated to give a gum. Flash chromatography (SiO$_2$/2–16% ethyl acetate-hexane) afforded the title compound (0.297 g, 70%) as a yellow solid: $^1$H NMR (acetone-d$_6$, 400 MHz) δ9.11 (dd, J=11.0, 8.5 Hz, 1H), 8.95 (dd, J=11.0, 8.5 Hz, 1H), 7.94 (m, 1H), 7.46 (m, 2H), 7.37 (m, 4H), 6.84 (t, J=7.3 Hz, 1H), 6.69 (m, 2H), 6.57 (d, J=8.5 Hz, 1H), 6.43 (br s, 2H), 4.92 (d, J=11.4 H 1H), 4.74(d, J=11.4 Hz, 1H), 4.69 (s, 1H), 4.58 (s, 1H), 4.40 (d, J=11.8 Hz, 4.26 (d, J=5.5 Hz, 2H), 3.99 (d, J=11.8 Hz, 1H), 3.25 (m, 1H). MS (ESI$^-$) m/e 704 (M–H)$^-$.

EXAMPLE 5

2, 3, 9, 10-Tetrafluoro-12-(2, 3, 4-tri-O-benzyl-6-deoxy-5, 6-anhydro-β-D-glucopyranosyl)-6, 7, 12, 13-tetrahydro(5H)indolo[2, 3-a]pyrrolo[3, 4-c]carbazole-5, 7-dione

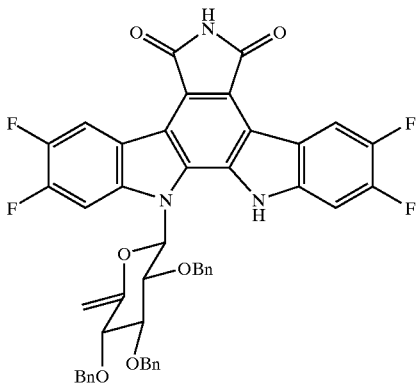

Prepared as described for Example 4 as a yellow solid in 78% yield: $^1$H NMR (CDCl$_3$, 400 MHz) δ9.38 (s, 1H), 9.13 (t, J=9.3 Hz, 1H), 8.99 (t, J=Hz, 1H), 7.56–7.41 (m, 6H), 7.29 (m, 2H), 6.90 (t, J=7.1 Hz, 1H), 6.74 (t, J=Hz, 2H), 6.68 (d, J=7.9 Hz, 1H), 6.43 (d, J=7.2 Hz, 3H), 5.06 (m, 2H), 4.84 (d, J=11.6 Hz, 1H), 4.74 (d, J=1.3 Hz, 1H), 4.68 (d, J=10.1 Hz, 1H), 4.58–4.54 (m, 2H), 4.19 (m, 1H), 3.94 (d, J=11.4 Hz, 1H). MS (ESI$^-$) m/e 810 (M–H)$^-$.

EXAMPLE 6

2, 3, 9, 10-Tetrafluoro-12-(4, 6-dideoxy-5-methoxy-β-D-glucopyranosyl) -6, 7, 12, 13-tetrahydro(5H)indolo[2, 3-a]pyrrolo[3, 4-c]carbazole-5, 7-dione

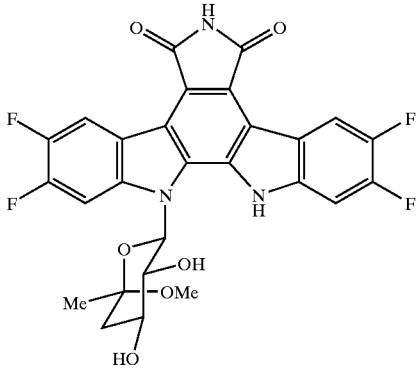

A solution of 2, 3, 9, 10-tetrafluoro-12-(2, 3-di-O-benzyl-4, 6-dideoxy-5, 6-anhydro-β-D-glucopyranosyl)-6, 7, 12, 13-tetrahydro(5H)indolo[2, 3-a]pyrrolo[3, 4-c]carbazole-5, 7-dione (0.100 g, 0.14 mmol) in 10 mL of dichloromethane was cooled at −78° C. under Ar and a solution of BBr$_3$ (1 M in CH$_2$Cl$_2$, 1.12 mL, 1.12 mmol) was added. The reaction mixture was kept at −78° C. for 1 h and then it was quenched with methanol (1 mL) and subsequently evaporated to dryness. The resulting residue was purified by prep. tlc (20 cm×20 cm×0.5 mm SiO$_2$ plates/THF-hexane, 1:1; triple development) to give the title compound (0.064 g, 87%) as a yellow solid: IR(KBr) 1752, 1717, 1476cm$^{-1}$. $^1$H NMR (THF-d$_8$, 400 MHz) δ10.42 (s, 1H), 10.15 (br s, 1H), 9.16 (m, 1H), 9.05 (m, 1H), 7.83–7.55 (m, 2H), 6.23 (d, J=9.4 Hz, 0.3H), 6.03 (d, J=9.0 Hz, 0.7H), 4.74–4.26 (m, 2H), 4.12 (m, 1H), 3.77 (m, 1H), 3.45 (s, 3H), 2.35–2.00 (m, 2H), 1.88 (s, 3H). MS (ESI$^-$) m/e 556 (M−H)$^-$. HPLC: 99.1% (320 nm).

EXAMPLE 7

2, 3, 9, 10-Tetrafluoro-12-(5-methoxy-β-D-glucopyranosyl)-6, 7, 12, 13-tetrahydro(5H)indolo[2, 3-a]pyrrolo[3, 4-c]carbazole-5, 7-dione

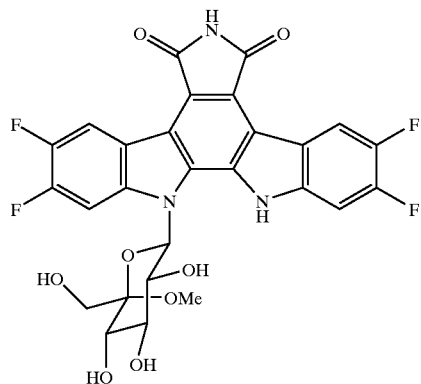

To a solution of 2, 3, 9, 10-tetrafluoro-12-(2, 3, 4-tri-O-benzyl-6-deoxy-5, 6-anhydro-β-D-glucopyranosyl)-6, 7, 12, 13-tetrahydro(5H)indolo[2, 3-a]pyrrolo[3, 4-c]carbazole-5, 7-dione (0.160 g, 0.20 mmol) in 5 mL of dichloromethane, at 0° C. under Ar, was added an ice-cold solution of dimethyldioxirane (ca. 0.1 M in acetone, 6.0 mL, 0.60 mmol). The resulting mixture was kept at 0° C. for 1.5 h and then it was evaporated in vacuo to give a yellow gum.

A portion of this gum (0.020 g, 0.024 mmol) was taken up in dichloromethane (2 mL) and then zinc chloride (1 M in diethyl ether, 0.050 mL, 0.050 mmol) was added, followed by methanol (0.10 mL). The resulting mixture was stirred at room temperature for 18 h and then it was evaporated to dryness to give a yellow gum: MS (ESI$^-$) m/e 858 (M−H)$^-$.

The crude gum was taken up in methanol (5 mL), Pearlman's catalyst (0.010 g) was added and the mixture was hydrogenated at 1 atm for 2 h. The mixture was then filtered and the filter-cake was washed with THF. The filtrate was then evaporated and the residue purified by prep tlc (20 cm×20 cm×0.5 mm SiO$_2$ plates/THF-hexane, 4:1) to give the title compound (0.00058 g, 4% overall yield) as a yellow solid: $^1$H NMR (acetone-d$_6$, 400 MHz) δ9.13 (t, J=11.3 Hz, 1H), 9.00 (t, J=11.2 Hz, 1H), 7.96 (m, 1H), 7.61 (dd, J=6.8, 6.5 Hz, 1H), 6.19 (d, J=9.3 Hz, 1H), 4.30 (d, J=9.4 Hz, 1H), 4.21 (d, J=10.8 Hz, 1H), 4.13 (d, J=10.5 Hz, 1H), 4.03 (t, J=8.9 Hz, 1H), 3.83 (t, J=8.7 Hz, 1H), 3.29 (s, 3H). MS (ESI$^-$) m/e 588 (M−H)$^-$. HPLC: 95.8% (320 nm).

EXAMPLE 8

2, 3, 9, 10-Tetrafluoro-12-(4-deoxy-5-methoxy-β-D-glucopyranosyl) -6, 7, 12, 13-tetrahydro(5H)indolo[2, 3-a]pyrrolo[3, 4-c]carbazole-5, 7-dione

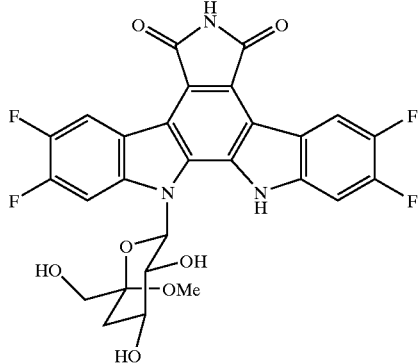

To a solution of 2, 3, 9, 10-tetrafluoro-12-(2, 3, 6-tri-O-benzyl-β-D-galactopyranosyl)-6, 7, 12, 13-tetrahydro(5H)indolo[2, 3-a]pyrrolo[3, 4-c]carbazole-5, 7-dione (0.606 g, 0.73 mmol) in 20 mL of dry dichloromethane was added (diethylamino)sulfur trifluoride (DAST) (0.50 mL, 3.66 mmol) dropwise at −45° C. under Ar. The reaction mixture was then stirred at room temperature for 1 h before being recooled at −45° C. and quenched with MeOH (2 mL). The mixture was evaporated and the residue was filtered through a plug of silica gel (elution with hexane-ethyl acetate, 1:1). The filtrate was evaporated and the residue was taken up in 20 mL of CHCl$_3$-MeOH (1:1), to which was added a solution of anhydrous HCl (4 M in dioxane, 2.0 mL, 8.0 mmol) and 20% Pd(OH)$_2$/C (0.60 g). The resulting mixture was hydrogenated (balloon pressure) at room temperature for 4 days and then it was filtered through a plug of silica gel (elution with THF). The filtrate was evaporated and the residue was chromatographed (SiO$_2$/hexane-THF, 1:1) to give the title compound (0.080 g, 20%) as a yellow solid: $^1$H NMR (DMSO-d$_6$, 400 MHz) δ11.77 (s, 1H), 11.29 (s, 1H), 9.01 (dd, J=11.0, 0.5 Hz, 1H), 8.93 (dd, J=11.0, 8.5 Hz, 1H), 8.17 (dd, J=11.9, 6.8 Hz, 1H), 7.64 (dd, J=11.0, 7.1 Hz, 1H), 6.63 (m, 1H), 5.97 (d, J=9.1 Hz, 1H), 5.46 (d, J=5.8 Hz, 1H), 4.97 (d, J=5.8 Hz, 1H), 4.01 (m, 2H), 3.58 (m, 2H), 3.46 (s, 3H), 2.43 (m, 1H), 2.08 (m, 1H). MS (ESI$^-$) m/e 572 (M−H)$^-$. HPLC: 88.1% (320 nm).

EXAMPLE 9

3, 9-Difluoro-12-(4, 6-dideoxy-5-methoxy-β-D-glucopyranosyl)-6, 7, 12, 13-tetrahydro(5H)indolo[2, 3-a]pyrrolo[3, 4-c]carbazole-5, 7-dione

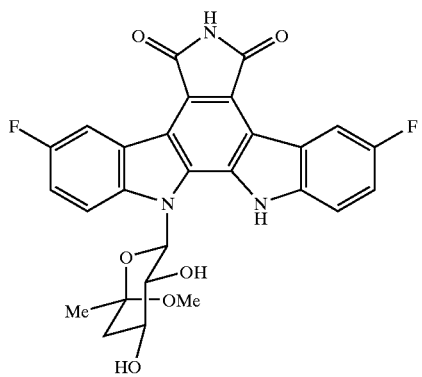

To a solution of 3, 9-difluoro-12-(2, 3-di-O-benzyl-4, 6-dideoxy-5, 6-anhydro-β-D-glucopyranosyl)-6, 7, 12, 13-tetrahydro(5H)indolo[2, 3-a]pyrrolo[3, 4-c]carbazole-5, 7-dione (0.091 g, 0.136 mmol) in 10 mL of methanol was added p-toluenesulfonic acid monohydrate (0.002 g, 0.01 mmol) and the mixture was stirred at room temperature for 17 h. Triethylamine (2 drops) was then added and the mixture was evaporated to dryness. The residue was taken up in dichloromethane and the solution was applied to a short silica gel column. Elution with dichloromethane-acetonitrile (95:5) afforded pure 3, 9-difluoro-12-(2, 3-di-O-benzyl-4, 6-dideoxy-5-methoxy-β-D-glucopyranosyl)-6, 7, 12, 13-tetrahydro(5H)indolo[2, 3-a]pyrrolo[3, 4-c]carbazole-5, 7-dione (0.075 g, 79%) as a yellow solid: MS (ESI⁻) m/e 700 (M−H)⁻.

A mixture of this compound and 20% Pd(OH)₂/C (0.114 g) in 20 mL of methanol was hydrogenated at 1 atm pressure for 18 h. The mixture was then filtered (Celite) and the filter-cake was washed with methanol and then THF. The filtrate was evaporated and the resulting yellow glass was purified on an LH-20 column, eluting with methanol. This afforded a residue which was triturated with a minimum volume of methanol to give the title compound (0.035 g, 67%) as an orange-yellow powder: ¹H NMR (THF-d₈, 400 MHz) δ10.82 (s, 0.35H), 10.42 (s, 0.65H), 10.14 (s, 0.65H), 10.09 (s, 0.35H), 9.07 (dd, J=2.5, 9.6 Hz, 0.35H), 9.03 (dd, J=2.9, 9.6 Hz, 0.65H), 8.97 (dd, J=2.5, 9.6 Hz, 0.65H), 8.93 (dd, J=2.5, 9.6 Hz, 0.35H), 7.94 (dd, J=4.3, 8.6 Hz, 0.35H), 7.78 (dd, J=4.1, 9.1 Hz, 0.65H), 7.72 (dd, J=4.3, 9.0 Hz, 0.65H), 7.67 (dd, J=4.1, 8.9 Hz, 0.35H), 7.37–7.24 (m, 2H), 6.28 (dd, J=2.0, 9.1 Hz, 0.35H), 6.13 (d, J=9.1 Hz, 0.65H), 5.53 (d, J=5.1 Hz, 0.35H), 4.76 (d, J=4.1 Hz, 0.65H), 4.61 (d, J=5.0 Hz, 0.65H), 4.51 (d, J=3.9 Hz, 0.35H) 4.33–3.68 (m, 2H), 3.44 (s, 3H), 2.50–1.82 (m, 2H), 1.79 (s, 3H). MS (ESI⁻) m/e 520 (M−H)⁻. HPLC: 100% (320 nm).

EXAMPLE 10

3, 9-Difluoro-12-(4, 6-dideoxy-5-ethoxy-6-D-glucopyranosyl)-6, 7, 12, 13-tetrahydro(5H)indolo[2, 3-a]pyrrolo[3, 4-c]carbazole-5, 7-dione

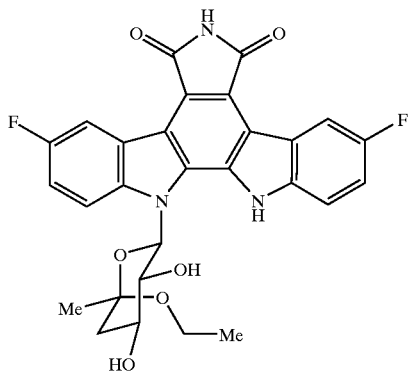

Prepared as for Example 9, except that ethanol was used as reaction solvent throughout. Final isolation was as a yellow lyophilate in 37% overall yield: ¹H NMR (THF-d₈, 400 MHz) δ10.53 (s, 0.3H), 10.46 (s, 0.7H), 10.12 (s, 0.7H), 10.07 (s, 0.3H), 9.03 (dd, J=2.5, 9.7 Hz, 1H), 8.91 (dd, J=2.6, 9.8 Hz, 1H), 7.92 (dd, J=4.4, 9.0 Hz, 0.3H), 7.68 (m, 1.7H), 7.54 (dd, J=3.2, 5.8 Hz, 0.3H), 7.37–7.26 (m, 1.7H), 6.33 (d, J=9.1 Hz, 0.3H), 6.15 (d, J=9.1 Hz, 0.7H), 4.75 (d, J=4.1 Hz, 1H), 4.61 (d, J=5.1 Hz, 1H), 4.23–3.64 (m, 4H), 2.46–1.88 (m, 2H), 1.80 (s, 3H), 1.33 (t, J=7.1 Hz, 3H). MS (ESI⁻) m/e 534 (M−H)⁻. HPLC: 97.9% (320 nm).

EXAMPLE 11

3, 9-Difluoro-12-(4, 6-dideoxy-5-isopropoxy-δ-D-glucopyranosyl)-6, 7, 12, 13-tetrahydro(5H)indolo[2, 3-a]pyrrolo[3, 4-c]carbazole-5, 7-dione

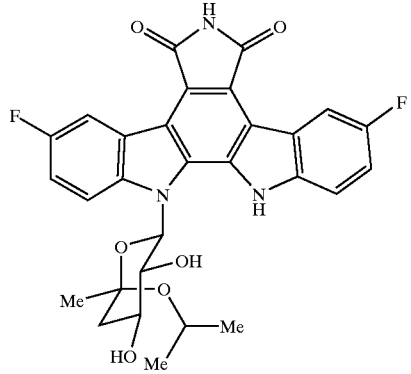

Prepared as for Example 9, except that isopropanol was used as reaction solvent throughout. Final isolation was as a yellow lyophilate in 43% overall yield: ¹H NMR (THF-d₈, 400 MHz) δ10.66 (s, 0.75H), 10.63 (s, 0.25H), 10.12 (s, 0.75H), 10.08 (s, 0.25H), 9.03 (dd, J=2.7, 9.6 Hz, 1H), 8.91 (dd, J=2.6, 9.7 Hz, 1H), 7.71 (dd, J=3.9, 9.0 Hz, 0.75H), 7.67 (m, 1.25H), 7.53 (dd, J=3.0, 5.6 Hz, 0.75H), 7.33 (m, 1.25H), 6.48 (d, J=9.3 Hz, 0.25H), 6.28 (d, J=9.2 Hz, 0.75H), 4.89 (d, J=4.0 Hz, 1H), 4.69 (d, J=5.0 Hz, 1H), 4.24–3.86 (m, 3H), 2.43–2.16(m, 2H), 1.85 (s, 3H), 1.25 (d, J=6.0 Hz, 2.25H), 1.21 (d, J=6.0 Hz, 2.25H), 1.07 (d, J=6.1 Hz, 0.75H), 0.97 (d, J=0.75H). MS (ESI⁻) m/e 548 (M−H)⁻. HPLC: 94.9% (320 nm).

EXAMPLE 12

2, 3, 9, 10-Tetrafluoro-12-(4, 6-dideoxy-5-methoxy-δ-D-glucopyranosyl)-6, 7, 12, 13-tetrahydro(5H)benzo[b]thieno[2, 3-a]pyrrolo[3, 4-c]carbazole-5, 7-dione

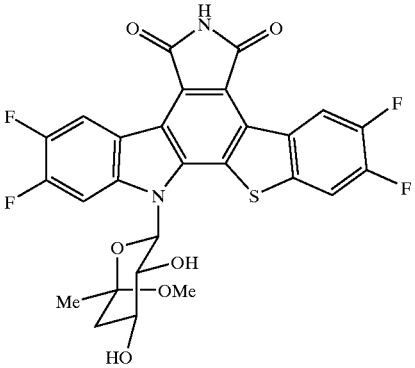

Prepared as for Example 9 and isolated as a yellow lyophilate in 70% overall yield: IR (KBr) 3433, 1709, 1475 cm⁻¹. ¹H NMR (THF-d₈, 400 MHz) δ10.52 (s, 1H), 10.06 (dd, J=8.1, 13.1 HZ, 1H), 9.28 (dd, J=8.6, 1 1.1 Hz, 1H), 8.11 (dd, J=7.6, 10.1 Hz, 1H), 7.90 (dd, J=7.1, 11.1 Hz, 1H), 6.55 (d, J=8.6 Hz, 1H), 4.78 (d, J=4.5 Hz, 1H), 4.55 (br s, 1H), 4.20–4.02 (m, 2H), 3.41 (s, 3H), 2.33–1.98 (m, 2H), 1.55 (s, 3H). MS (ESI⁻) m/e 573 (M−H)⁻. HPLC: 99.5% (320 nm).

Biological Activity

The compounds of the present invention are useful pharmacologic agents with anti-tumor properties. With topoisomerase I active properties, the compounds can be useful as anti-tumor agents. In recent years, numerous reports have appeared in the literature suggesting that the role of topoisomerase I targeting drugs is to stabilize a covalent DNA-topoisomerase I complex to yield enzyme-linked DNA single-strand breaks. From a pharmacologic standpoint, there are advantages to target Topoisomerase I; first, its occurrence at relatively high levels in both proliferating and quiescent cells suggests that its function may be independent of cellular growth rate, and; second, topoisomerase I active agents may be effective in slow-growing as well as rapidly proliferating tumors. Cells from colon tumors have been shown to contain higher intracellular levels of topoisomerase I than normal mucosal cells, suggesting the possibility for a selective cytotoxic advantage. Thus, inhibition of proliferation of tumor cells by compounds of the present invention was initially demonstrated by effective inhibition of human topoisomerase I. Certain compounds of the invention, usually having $EC_{50}$ values less than 10 μM in the topoisomerase I assay, were also tested in an inhibition of human/mouse tumor cell proliferation assay.

Topoisomerase I Activity (In Vitro)

Topoisomerase I activity was measured as described below. The procedure for assaying compound-induced, topoisomerase I-mediated single strand breaks in DNA was essentially that described by Hsiang, et al., (J. Biol. Chem. 1985, 260,14873–14878). Samples dissolved in 100% DMSO as either 10 μM or 10 mg/ml solutions, unless otherwise stated, were diluted in Tris-EDTA buffer. Marine bacteriophage PM2 DNA (Boehringer Mannheim) was also diluted in Tris-EDTA buffer to a concentration of 0.02 μg/μl. Different dilutions of compound being evaluated were mixed with diluted DNA and this mixture was added to 1000 unit (one unit of enzyme activity is defined as the amount capable of relaxing 100 ng of supercoiled DNA in approximately 30 minutes at 37° C.) aliquots of purified human topoisomerase I (Topogen) in 2×reaction buffer to start the reaction. The compound—DNA—enzyme mixture was incubated for 30 minutes at 37° C. before stopping the reaction with warm stop buffer containing sodium dodecyl sulfate and proteinase K (Sigma). These mixtures were allowed to incubate at 37° C. for another 10 minutes, at which time the mixtures were removed from the waterbath and extracted with a 24:1 mixture of chloroform/isoamyl alcohol. Following centrifugation, aliquots of the aqueous phases were placed in wells of a 0.9% agarose (SeaKem) gel in Tris-borate buffer containing 0.5 μg/ml of ethidium bromide and subjected to electrophoresis for 15 hours to separate the different topological isomers and nicked and broken DNAs. After destaining the gel in water, the ethidium bromide stained DNA reaction products were visualized by exposing the gel to UV irradiation. Negatives of photographs of the irradiated gels were scanned with a densitometer and areas under the peaks were calculated in order to obtain percent single strand DNA break formation for each sample. A median effective concentration ($EC_{50}$) was obtained for each compound by interpolation between points of the resulting dose-effect curve which defines the potency of the compound for its effect in inducing topoisomerase I-mediated single strand breaks in DNA. The topoisomerase I activity for selected compounds of the present invention is shown below in Table I.

TABLE I

| Example No. | $EC_{50}$ (μM) |
|---|---|
| 1 | 0.04 |
| 6 | 0.07 |
| 7 | 0.27 |
| 8 | 0.05 |

The novel compounds of the present invention, as exemplified by substituted sugar derivatives in Table I, show significant topoisomerase I activity.

Cell-Based Cytotoxicity Activity (In Vitro)

The proliferation inhibition activity against murine P388 cell line was measured as follows. Evaluation of a soluble tetrazolium/formazan assay for cell growth and drug sensitivity in culture, using human and other tumor cell lines, was done according to the procedure described in Cancer Res. 1988, 48, 4827–4833. Cells were plated at 4000 cells/well in 96 well microtiter plates and 24 h later drugs were added and serially diluted. The cells were incubated at 37° C. for 72 h, at which time a tetrazolium dye, XTT, containing phenazine methosulfate was added. A dehydrogenase enzyme in live cells reduced the XTT to a form that absorbs light at 450 nm, which could be quantitated spectrophotometrically. The greater the absorbance the greater the number of live cells. The results are expressed as an $IC_{50}$, which is the drug concentration required to inhibit cell proliferation (i.e., absorbance at 450 nm) to 50% of that of untreated control cells. The results for selected compounds of the present invention are shown in Table II.

TABLE II

| Example No. | $IC_{50}$ (μM) |
|---|---|
| 1 | 0.035 |
| 6 | 0.050 |
| 7 | 0.25 |
| 8 | 0.035 |
| 9 | 0.007 |
| 10 | 0.055 |
| 11 | 0.20 |
| 12 | 0.069 |

What is claimed is:

1. A compound or pharmaceutically acceptable addition salt or solvate thereof, useful for inhibiting topoisomerase I and the proliferation of tumor cells selected from the group consisting of:

a.

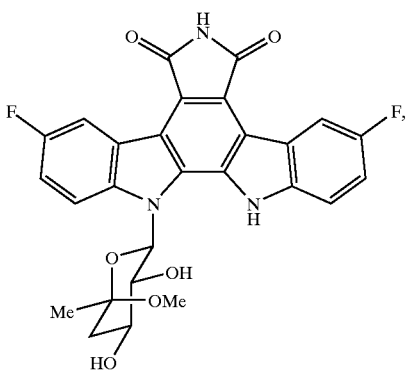

-continued
b.
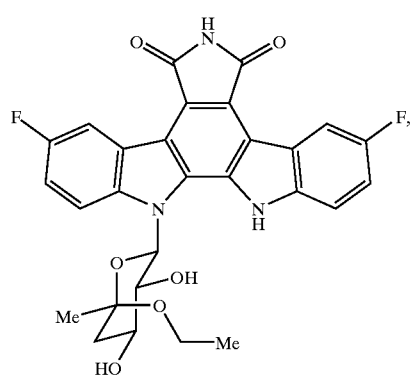
c.
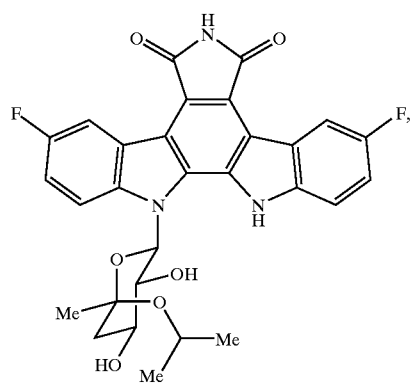
d.
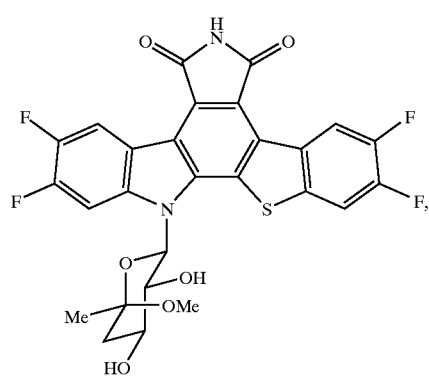
e.
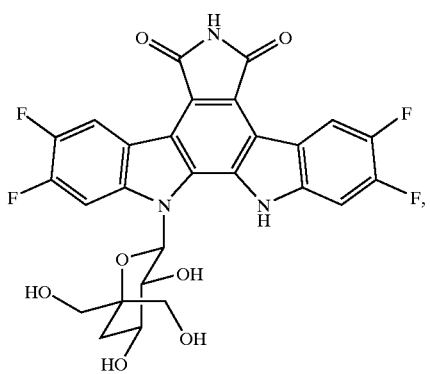
-continued
f.
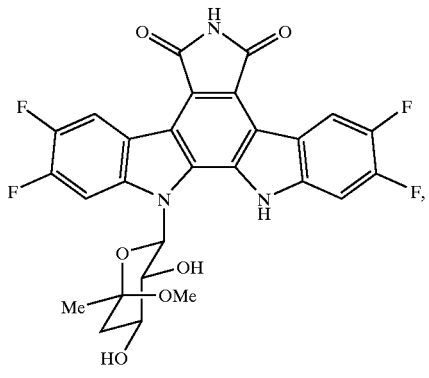
g.
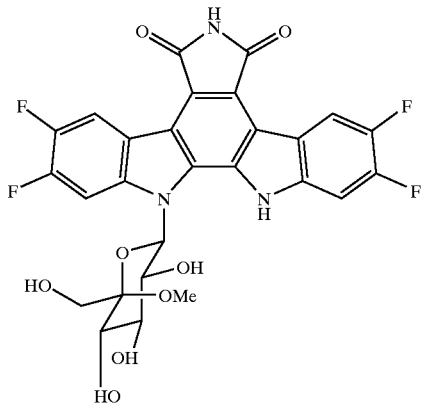 and
h.
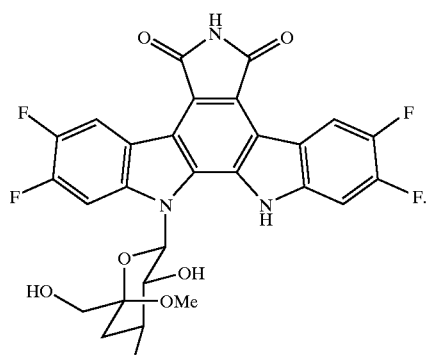
* * * * *